(12) United States Patent
Crowther et al.

(10) Patent No.: US 7,862,507 B2
(45) Date of Patent: Jan. 4, 2011

(54) CONFOCAL RAMAN SPECTROSCOPY FOR DERMATOLOGICAL STUDIES

(75) Inventors: Jonathan Mark Crowther, Egham (GB); Peter Blenkiron, Egham (GB); Paul Jonathan Matts, Addlestone (GB); Anke Sieg, Englefield Green (GB)

(73) Assignee: The Procter & Gamble Company, Cincinnati, OH (US)

( * ) Notice: Subject to any disclaimer, the term of this patent is extended or adjusted under 35 U.S.C. 154(b) by 1164 days.

(21) Appl. No.: 11/510,898

(22) Filed: Aug. 28, 2006

(65) Prior Publication Data
US 2007/0049831 A1 Mar. 1, 2007

(30) Foreign Application Priority Data
Aug. 31, 2005 (EP) ................................. 05018928

(51) Int. Cl.
*A61B 5/00* (2006.01)
*A61B 6/00* (2006.01)
*A61B 5/103* (2006.01)

(52) U.S. Cl. .................. 600/306; 600/476; 600/587

(58) Field of Classification Search ............... 600/306, 600/300, 473–480, 587
See application file for complete search history.

(56) References Cited

U.S. PATENT DOCUMENTS

| | | | |
|---|---|---|---|
| 6,069,689 A | | 5/2000 | Zeng |
| 6,070,093 A | * | 5/2000 | Oosta et al. ............... 600/316 |
| 6,289,230 B1 | * | 9/2001 | Chaiken et al. ........... 600/322 |
| 6,352,502 B1 | * | 3/2002 | Chaiken et al. ........... 600/473 |
| 6,353,226 B1 | * | 3/2002 | Khalil et al. .............. 250/341.8 |
| 6,503,478 B2 | * | 1/2003 | Chaiken et al. ........... 424/9.1 |
| 6,567,678 B1 | * | 5/2003 | Oosta et al. ............... 600/316 |
| 6,681,133 B2 | * | 1/2004 | Chaiken et al. ........... 600/473 |
| 2002/0041848 A1 | * | 4/2002 | Chaiken et al. ........... 424/9.1 |
| 2002/0091322 A1 | * | 7/2002 | Chaiken et al. ........... 600/476 |
| 2004/0106163 A1 | * | 6/2004 | Workman et al. .......... 435/14 |
| 2004/0185430 A1 | | 9/2004 | Lefebvre |
| 2006/0004306 A1 | * | 1/2006 | Altshuler et al. .......... 601/3 |
| 2007/0020181 A1 | * | 1/2007 | Workman et al. .......... 424/9.1 |

(Continued)

FOREIGN PATENT DOCUMENTS

EP 1 314 395 A2 5/2003

OTHER PUBLICATIONS

"Automated depth-scanning Confocal Raman microspectrometer for rapid in vivo determination of water concentration of water concentration profile in human skin", P.J. Caspers, G.W. Lucassen, H.A. Bruining and G. J. Puppels, *J. Raman Spectrosc. 31*, 813-818 (2000).

(Continued)

*Primary Examiner*—Charles A Marmor, II
*Assistant Examiner*—Navin Natnithithadha
(74) *Attorney, Agent, or Firm*—Megan C. Hymore; Eric T. Addington (57) ABSTRACT

Use of Confocal Raman Spectroscopy (CRS) for dermatological studies, including a method for determining the thickness of the Stratum Corneum (SC) on a test area of the skin, and to a method for quantifying the effectiveness of a skin care composition. The methods of the invention can be carried in vitro (either artificial skin or a sample of skin) or in vivo (directly on the human skin of a person).

14 Claims, 4 Drawing Sheets

U.S. PATENT DOCUMENTS

2007/0049831 A1* 3/2007 Crowther et al. ............ 600/473
2007/0050202 A1* 3/2007 Crowther et al. ............... 705/1

OTHER PUBLICATIONS

"In vivo Confocal Raman Microspectroscopy of the Skin: Noninvasive Determination of Molecular Concentration Profiles", P.J. Caspers, G.W. Lucassen, E. A. Carter, H.A. Bruining and G. J. Puppels, *The Journal of Investigative Dermatology*, vol. 133, No. 3 Mar. 2001, 434-442.

"Confocal Raman Microscopy for Cosmetic Applications", published in "Raman Update", a publication by Horiba Jobin Yvon, Winter Edition 2005.

"Combined In Vivo Confocal Raman Spectroscopy and Confocal Microscopy of Human Skin", P.J. Caspers, G.W. Lucassen and G.J. Puppels, *Biophysical Journal*, vol. 85, Jul. 2003, 572-580.

"Stratum Corneum Swelling. Biophysical and Computer Assisted Quantitative Assessments", Lars Norlén, Axel Emilson, Bo Forslind, *Archives of Dermatological Research*, vol. 289, 1997, 506-513.

In Vivo Chemical Investigation of Human Skin Using A Confocal Raman Fiber Optic Microprobe; L. Chrit, C.Hadjur, S. Morel, G. Sockalingum, G. Lebourdon, F. Leroy, M. Manfait; Journal of Biomedial Optics; Jul./Aug. 2005 vol. 10(4), 1-11.

In Vitro and In Vivo Raman Spectroscopy of Human Skin, P.J. Caspers, G.W. Lucassen, R. Wolthius, H.A. Bruining and G.J. Puppels, Biospectroscopy, vol. 4, 1998, S31-S39.

PCT International Search Report Dated Feb. 6, 2007, 4 pages.

* cited by examiner

CONFOCAL RAMAN SPECTROSCOPY FOR DERMATOLOGICAL STUDIES

FIELD OF THE INVENTION

The present invention relates to the use of Confocal Raman Spectroscopy (CRS) for dermatological studies. In particular, the invention relates to a method for determining the thickness of the Stratum Corneum (SC) on a test area of the skin, and to a method for quantifying the effectiveness of a skin care composition. The methods of the invention can be carried in vitro (either artificial skin or a sample of skin) or in vivo (directly on the human skin of a person).

BACKGROUND OF THE INVENTION

Skin is composed of two main layers, the dermis and epidermis, which are in turn composed of sub-layers. The surface of the skin is the outermost layer of the epidermis and is called the Stratum Corneum. It is composed mainly of dead cells that lack nuclei and contain keratin, a protein that helps keep the skin hydrated by preventing water evaporation. In addition, these cells can also absorb water.

The standard method for measuring skin hydration in the Stratum Corneum is to measure a change in the electrical properties of the skin (specifically the capacitance), which is related to the degree of hydration. The apparatus commonly used for this measurement is called a Corneometer® (available from Courage & Khazaka).

Water has a very high dielectric constant, closely followed by glycerine, both higher than the dry skin values. Therefore it is assumed that an increase in Corneometer values can be equated with an increase in moisturization (mainly due to a water effect, however contributions from glycerine cannot be ruled out). However the scale is not linear, and therefore the technique is not quantitative. Also the depth over which the data is collected is poorly defined. Although the depth range is believed to cover the entire Stratum Corneum it may well cover a portion of the viable epidermis as well. With this technique it is also not possible to get information on the distribution of water within the stratum corneum, with only a single number being generated per reading. In addition, alternative ways of making such measurements must often be made by invasive methods.

The present invention uses a different technique to measure skin moisturization, based on Confocal Raman Spectroscopy. Raman spectroscopy is the measurement of the wavelength and intensity of inelastically scattered light from molecules. Raman scattered light occurs at wavelengths that are shifted from the incident light by the energies of molecular vibrations. The mechanism of Raman scattering is different from that of infrared absorption, and Raman and IR spectra provide complementary information. For further background information on Raman spectroscopy, see for example "Fundamentals of Molecular Spectroscopy", C. N. Banwell, McGraw Hill, 1983.

Two of the major advantages of Raman Spectroscopy are the non destructive nature of this technique and the virtually no need for sample preparation that it requires, which may provide significant cost and time savings.

Confocal optics relate to the illumination of a sample with a diffraction limited spot such that the illuminating spot is imaged on an ideally point-like detector, the point-like detector being realised with an adjustable pinhole called 'confocal hole' in front of the real detector (entrance slit). An advantage of confocal sampling is the ability to separate the signal from each layer of a layered sample. In the case of skin measurement, Confocal Raman Microspectroscopy allows to measure the property of skin as a function of depth.

It has been recently proposed to apply Raman Microspectroscopy to the analytical determination of skin moisturization, see:

"Automated depth-scanning Confocal Raman microspectrometer for rapid in vivo determination of water concentration of water concentration profile in human skin", P. J. Caspers, G. W. Lucassen, H. A. Bruining and G. J. Puppels, *J Raman Spectrosc.* 31, 813-818 (2000);

"In vivo Confocal Raman Microspectroscopy of the Skin: Noninvasive Determination of Molecular Concentration Profiles", P. J. Caspers, G. W. Lucassen, E. A. Carter, H. A. Bruining and G. J. Puppels, *The Journal of Investigative Dermatology*, Vol. 133, No. 3 March 2001, 434-442;

"Confocal Raman Microscopy for Cosmetic Applications", published in "Raman Update", a publication by HORIBA Jobin Yvon, Winter Edition 2005.

Although some of the above mentioned documents have recognized the usefulness of Confocal Raman Spectroscopy to study the profile of hydration within the Stratum Corneum as a function of depth, as well as a function of time (for example pre- and after-application of a skin moisturization composition), the inventors have made the surprising discovery that, in some cases, the data measured by this advanced technique leads to incoherent results, as is discussed below.

Whilst making measurements of skin hydration of the Stratum Corneum, the inventors found that, unexpectedly, the hydration value as measured by Confocal Raman Spectroscopy at a specific depth within the Stratum Corneum decreased after the application of certain skin care hydration products. These results contradicted visual examination of the surface of the area of the skin tested as well as Corneometer measurements, which indicated an overall increase in skin hydration at the surface of the skin area. After further experimentation and insight, and whilst not wishing to be bound by theory, the inventors have come to the conclusion that certain skin care products can be so beneficial to the health of the skin that they increase the absolute depth of the Stratum Corneum of the users.

As will be discussed in details further below, the inventors have then found that in order to determine the effectiveness of skin care compositions a crucial factor that was previously overlooked is the evolution of the thickness of the Stratum Corneum. In addition to this insight, the inventors have developed a method for determining the thickness of the Stratum Corneum using Confocal Raman Spectroscopy. Traditionally the thickness of the Stratum Corneum has been measured by using biopsies, however this is an inherently destructive process, requiring removal of a section of flesh from the body.

SUMMARY OF THE INVENTION

A first aspect of the invention is a method for determining the thickness of the Stratum Corneum on a test area of skin using Confocal Raman Spectroscopy. The method comprises the steps of:

(a) measuring the concentration profile of a Raman-active material (for example water) as a function of depth within the test area using Confocal Raman Spectroscopy; then (b) processing the data obtained to determine the thickness of the Stratum Corneum.

A second aspect of the invention is for a method for determining the effectiveness of a skin care composition. The method uses the thickness of the Stratum Corneum (preferably as determined by the method of the first aspect of the invention) before and after application of the skin care composition as a parameter to quantify the effectiveness of the composition.

The method may comprise the steps of:
(i) selecting a Raman-active substance linked to the effectiveness of the skin care composition to be determined;
(ii) measuring the concentration profile of said Raman-active substance as a function of depth within a test area of skin using Confocal Raman Spectroscopy;
(iii) determining the thickness of the Stratum Corneum within said test area; then
(iv) applying the skin care composition to said test area; then
(v) measuring the concentration profile of said Raman-active substance as a function of depth within said test area using Confocal Raman Spectroscopy;
(vi) determining the thickness of the Stratum Corneum within said test area; then
(vii) calculating the effectiveness of the skin care composition as a function of both:
the concentration profile of the Raman-active substance after and before the application of the skin care composition; and
the thickness of the Stratum Corneum after and before the application of the skin care composition.

Steps (i) and (ii), as well as (v) and (vi) can be performed in any order.

Another aspect of the invention is for an apparatus comprising a Confocal Raman Spectroscopy probe and a computer, wherein the computer is programmed to process the data generated by the probe according to the methods of the invention.

DETAILED DESCRIPTION OF THE INVENTION

Confocal Raman Spectroscopy

Confocal Raman Spectroscopy uses a microscope system to focus laser light to a point. The light at the point of focus is of high intensity which is where the Raman signal is generated from. By altering the position of the microscope objective lens relative to the sample to be analysed, and when the sample is not completely opaque to the incident laser light the interior of the sample can be examined. By moving the objective lens in small increments a profile of Raman spectra as a function of depth can be produced. The Raman spectra contain peaks corresponding to the different functional groups of the chemicals present within the sample. The locations of these peaks are determined by the precise chemical structure of the components. Once the peak locations for different components of the sample are known, ratioing of one component to the others present can be carried out. For instance, % water in skin can be calculated by ratioing the amount of water and protein as calculated from the areas under the curves in the part of the spectra corresponding to water and protein respectively, and applying a proportionality constant (as detailed below).

Any suitable commercially available CRS equipment can be used. For example the inventors used a River Diagnostics Model 3510 Confocal Raman Microspectroscopy system (software version—RiverIcon v.1). This has been designed for use as an in-vivo, non invasive skin analysis device, enabling qualitative and semi-quantitative analysis of molecular concentrations and concentration profiles within the skin. The system incorporates a CCD detector combined with a microscope objective lens to enable focusing of the laser light into the skin and collection of the returning signal. 2 lasers are used—a 671 nm red laser for water profiling (operating in the high wavenumber region from 2500-4000 $cm^{-1}$), and a 785 nm near IR laser for low wavenumber region and natural moisturizing factor (NMF) measurement. Profiles in the high wavenumber region may be measured using 1 s acquisition times per spectra, and in the fingerprint using 10 s acquisitions per spectra. Typically 2 or 3 μm spacings between spectra may be used. The top few hundred microns of the skin is transparent to the light from both the 671 nm and 785 nm allowing profiling within the SC using this arrangement.

Figure 1:
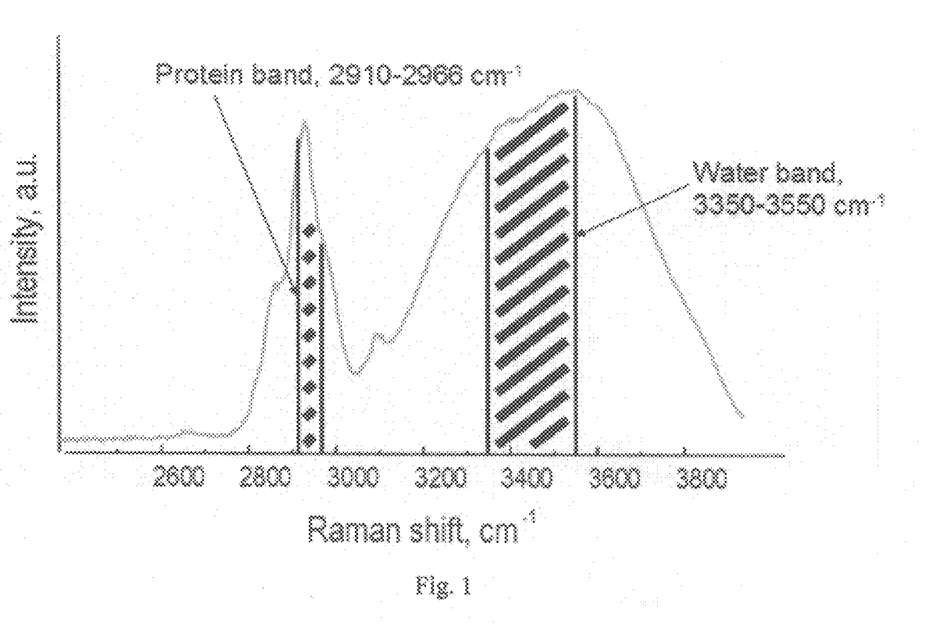
FIG. 1 shows a typical high wavenumber spectrum of hydrated skin and the relevant areas measured when determining the % hydration level.

The points forming the hydration profile as function of depth are derived by the software using the Raman spectra acquired for each depth value. The software may use the calculation method as outlined in Peter Caspers Ph.D. Thesis ('In-vivo skin characterization by confocal Raman spectroscopy', 2003, Erasmus University, Rotterdam, the Netherlands). For example, as explained in this thesis, the area between 3350-3550 $cm^{-1}$ may be integrated for the water band [water], and 2910-2966 $cm^{-1}$ for the protein band [protein] (a sample spectra showing the areas measured for water and protein is given in FIG. 1).

The percentage hydration may then be calculated for each depth with this formula:

$$\% \text{ hydration} = [\text{water}]/([\text{water}] + r \cdot [\text{protein}])$$

wherein r is a proportionality constant.

Figure 2:
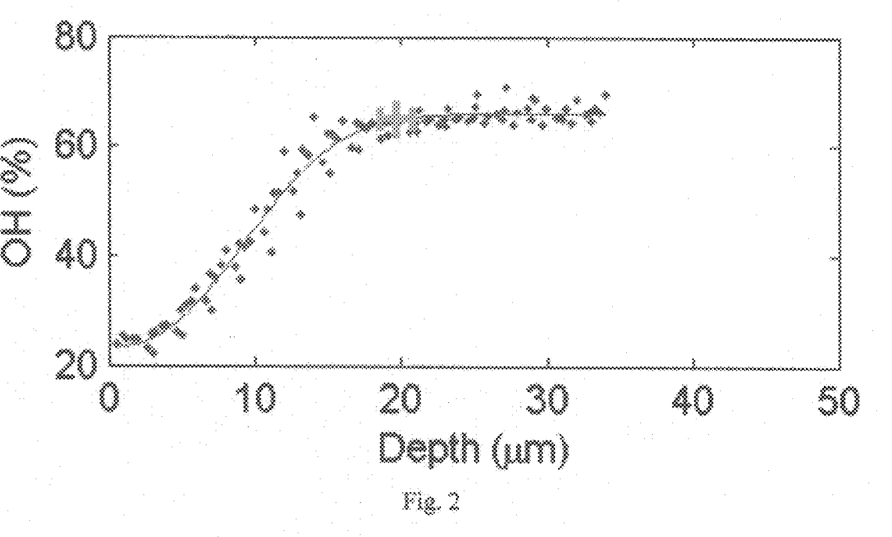
FIG. 2 shows a typical Confocal Raman Spectroscopy profile of the water content of skin as a function of depth. In this example, a typical water profile showing the surface of the stratum corneum at depth=0 with 20-30% hydration, rising to the 60-70% hydration within the body at a depth of approximately 20 μm for forearm skin. The line of best fit through the data points has been fit using a Weibull growth curve model.

This procedure is carried out automatically at each point of the spectra by the associated RiverIcon software and results in the formation of a hydration profile (see FIG. 2). A similar process may be followed when looking at different active species (for example vitamins, and amino acids), where a principal component analysis using well defined peak locations is used to calculate a profile for each of the ingredients of interest. Again this is carried out within the standard software provided with the equipment and the data outputted in the form of a profile for the ingredient of interest as a function of depth.

Raman Active Materials Present in Skin

In principle, anything which is Raman active can be measured within the skin using this technique. For a specific vibrational mode to be Raman active, there must be a change in the polarizability of the molecule caused by the vibration. It has already been shown in the literature (papers by Puppels and Caspers from River Diagnostics) that water and the amino acids which make up natural moisturizing factors (NMF) can be analyzed within the skin, along with cholesterol, lactic acid, and keratin. Due to the complex structure of most ingredients of interest within skin care formulations there will normally be some vibrations associated with any given molecule of interest which will be Raman active. In order for the molecules of interest to be measured in a Raman profile they must fulfill two criteria, i) that they have peaks which are sufficiently distinct from other components within the skin, and ii) that the ingredient is present in sufficient quantity to be detected. The absolute intensity of the peaks in a spectrum will be determined by how strong the change in polarizability is, and will vary from compound to compound. Peak location within the spectrum is determined by the functional groups present within the molecule.

Treatment of the Data

The data points gathered are processed to be more readily usable. Data points that make up each profile may be saved as a tab delimited text file and imported into a suitable mathematical software, for example Matlab. In the exemplary system used, up to 8 profiles for any given site may be imported. The dataset (containing all profiles) may then be treated as a cloud of points through which a line of best fit is put. The mathematical model for the line of best fit may be based on the Weibull model, although different models may be used (e.g. polynomial regression).

The Weibull distribution is widely used in reliability and life (failure rate) data analysis and as a biological growth model. The equation for the Weibull model used here is given below.

$$y=a-(a-b)*\exp(-(x/c)^d)$$

Where a, b, c and d are variables determined during the optimization of the line of best fit by the mathematical software. A line of best fit based upon this model is fitted to the dataset (see FIG. 2), and using this equation different parameters of the skin can be determined (for example, bottom of the stratum corneum (SC), complete area under the curve from the surface to the base of the SC).

Determination of the Thickness of the Stratum Corneum

During the calculation of the line of best fit through the dataset, the determination of the leveling off point of the curve is also carried out. The leveling off point is determined using a gradient threshold on the Weibull model. A value for the gradient threshold may be set by the operator during data analysis. The leveling off point is taken as where the slope on the modeled curve matches the threshold set. This leveling off point corresponds to where the water rich living tissue of the epidermis meets the SC, i.e. the bottom of the SC.

When analyzing an entire study, a subset of the data is chosen at random and analysed using different gradient threshold values, the operator then determines the most accurate fit for the leveling off point and uses the corresponding gradient threshold value for analysis of the entire study. The need for operator choice for the gradient threshold arises from a number of factors. For example the skin on different body parts has inherently different water profiles, also the skin's natural hydration state is strongly influence by the time of year and associated weather conditions. It should be emphasized though, that once a value for the gradient threshold has been derived for the small subset of data from the entire study, that value is normally used for the entire analysis. Typical values for the gradient threshold on volar forearm skin are between 0.4 and 1.0, and this range may be used as a starting point when determining the appropriate value. An example data set fitted with the Weibull model is shown in FIG. 2. It is also be possible to use other mathematical operations to determine the leveling off point, such as the point at which the % hydration reaches a fixed percentage of the upper asymptote of the Weibull model. As with the use of the gradient threshold, this provides a route to determining the location of the bottom of the SC.

Determination of the Effectiveness of a Skin Care Composition

The effectiveness of a skin care composition is normally expressed as the change of a certain skin quality between the beginning and the end of the study. Confocal Raman Spectroscopy may be used to quantify the change of concentration of a Raman active material within the skin, and therefore may be used to determine the effectiveness of a skin care composition when a Raman active material can be linked the effect of the composition studied. For example, a change in skin hydration, which can be linked to the concentration of water within the skin, can be measured using the CRS technique because water is a Raman active material. Similarly, any Raman active materials that can be linked to the effectiveness of a skin care composition (Natural Moisturizing Factors (NMF), Vitamins, etc. . . . ) may also be used to quantify its effectiveness.

The term "skin care composition" as used herein refers to a product that is intended to have an effect on skin. The term includes cosmetic product, whose purpose to improve the appearance of skin, as well as therapeutic treatment, whose purpose is to prevent or treat a skin disease (these terms are not mutually exclusive). Non-limiting examples of skin-care products include leave-on products (e.g. moisturizing creams, self-tanning products, tinted moisturizers, powders, foundations, conditioning wipes, etc.) and rinse-off products (shower gels, in-shower moisturizers, foaming wipes, etc.). Also included are products which are not directly applied on the skin, e.g. nutraceuticals which are ingested by the user.

The inventors have now found that for effectively quantifying the effectiveness of a skin care composition using Confocal Raman Spectroscopy, it is important to take into account the change of thickness of the SC during the study. Without wishing to being bound by theory, this may be because changes in the hydration state of the skin alter its thickness, or that certain skin actives (e.g. Niacinamide) may increase skin cells proliferation. Therefore it may not be appropriate to compare values obtained at the beginning and the end of the study at a constant depth (e.g. 10 μm).

For actives delivered from the composition, it is normally important to know depth of penetration and % concentration as a function of depth. As such it is important to reference any change in the quantity of a Raman active material % hydration changes to % of the way through the SC. Also as the thickness of the SC may have changed, the parameter of total area under the curve from the surface to the bottom of the SC becomes important as a total hydration measure. Wrongly considering that the SC to be fixed in thickness throughout the study may lead to incorrect interpretation of the data.

The thickness of the SC at the beginning and then at the end of the study may be determined using the method described above which employs a CRS technique. Measuring the water concentration profile using CRS and processing the data obtained was found to be a good way to determine SC thickness. If the effect to be measured is skin hydration, then only one measure of the concentration profile at the beginning and at the end of the study needs to be performed, because the data generated for determining the SC thickness can also be used to determine the water content of the SC.

There are different ways to express the effectiveness of a skin care composition using the data generated by CRS and the SC thickness, of which two preferred examples are outlined here:

- a specific relative depth of the SC (e.g. half-way) may be selected, and the amounts of Raman-active substance (e.g. water) linked to the effect of the skin care composition (e.g. skin hydration) to be determined at this relative depth at the beginning and at the end of the study may be compared;
- another way to express the effectiveness of the composition is to measure the area under the curve (integrating), between the skin surface and the end of SC (e.g. as determined by CRS, as described above). Dividing the value obtained for the surface area at the end of the treatment by the value obtained for the surface area at the beginning of the treatment gives a measure of the effectiveness of the composition in %. This method of quantifying the effect also works well for quantifying skin hydration. Also the total area under the curve for individual NMF's could be linked to health of the skin (as NMF's are beneficial to the water holding capability of the SC and are readily washed out).

EXAMPLE 1

Figure 3:
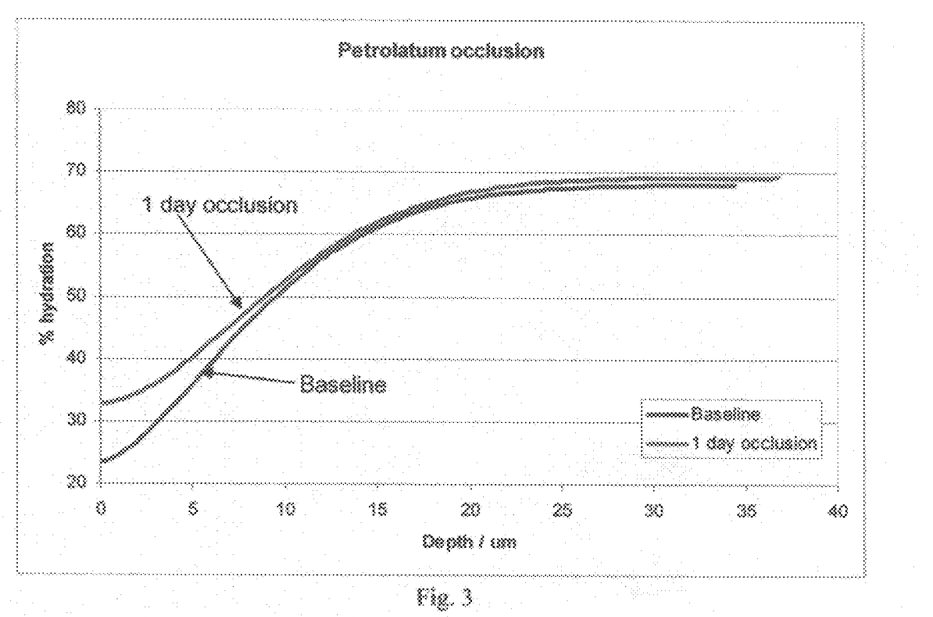
FIG. 3 shows the hydration profile before and after application of petrolatum.

Single Variable Analysis of Hydration Levels within the Skin—Petrolatum Occlusion To demonstrate the effects of a single variable on skin hydration, a set of baseline spectra were recorded (the site to be used was dry wiped to remove surface sebum before the measurements were taken). Petrolatum was then applied to the same area of the forearm 4 times over a 24 hour period with the aim of promoting skin hydration via occlusion. After 24 hours the site was dry wiped to remove any surface contamination and a further set of profiles collected (FIG. 3). This shows how the hydration level near the surface of the SC has increased due to occlusion (x=0 to 5 μm). Also the total area under the curve from the surface to the bottom of the SC has increased from 697 to 764—an increase of approximately 10%.

EXAMPLE 2

Effect of Moisturizing Products

In this study, two commercial moisturizing treatments ('a'—Olay® Quench, and 'b'—Jergens® Ultra Healing) were used. After an initial baseline reading product, the products were applied for 2 weeks followed by a 1 week regression period during which no product was applied to the sites examined. Product application was 2 μl cm$^{-2}$, twice daily, over sites on the volar forearms of 15 panelists. Panelists did not use moisturizing products other than those provided by the study organizers on their forearms over the entire course of the study. The baseline profile for skin hydration at the beginning of the study (no products applied) is shown on FIG. 4. As shown, the baseline profile for both sites 'a' and 'b' were identical.

Figure 5:
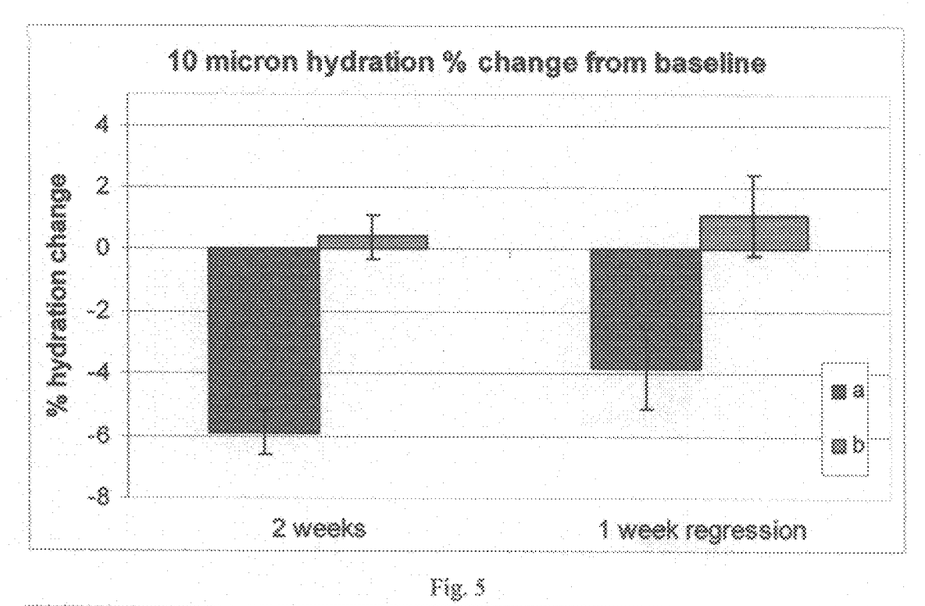
FIG. 5. shows change from baseline in % hydration measured at a fixed depth (10 μm) below the surface of the SC for both treatment regimes ('a' and 'b') during 2 weeks of product application and after 1 weeks regression.

The change in % hydration for the two moisturizing treatments 'a' and 'b' at the fixed depth of 10 μm data beneath the surface of the SC is given in FIG. 5. Looking at the data in FIG. 5, treatment 'a' appears to be resulting in a dehydration of the SC at 2 weeks usage and after 1 week regression.

Figure 4:
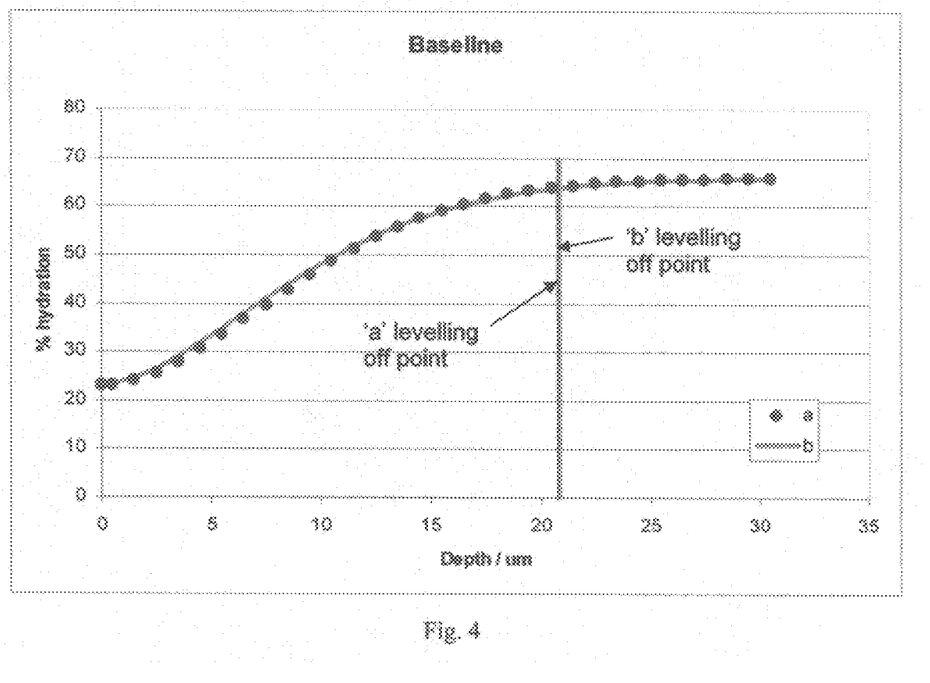
FIG. 4 shows the Raman hydration profiles (averaged across all subjects by treatment) before product application at the start of a study to compare two treatment regimes ('a' and 'b').
Figure 6:
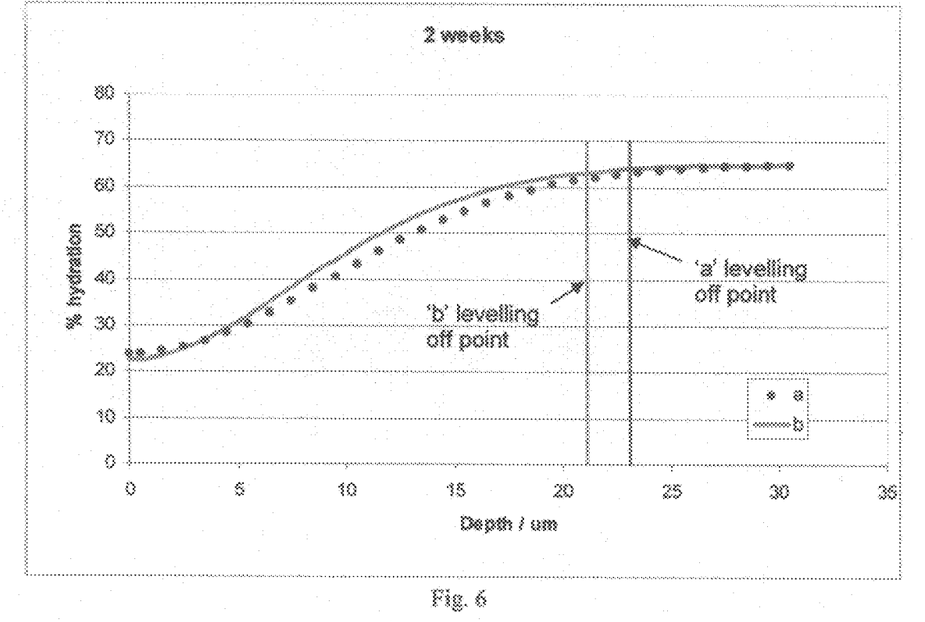
FIG. 6 shows the Raman hydration profiles (averaged across all subjects by treatment) after 2 weeks of product application for the treatment regimes 'a' and 'b'.
Figure 7:
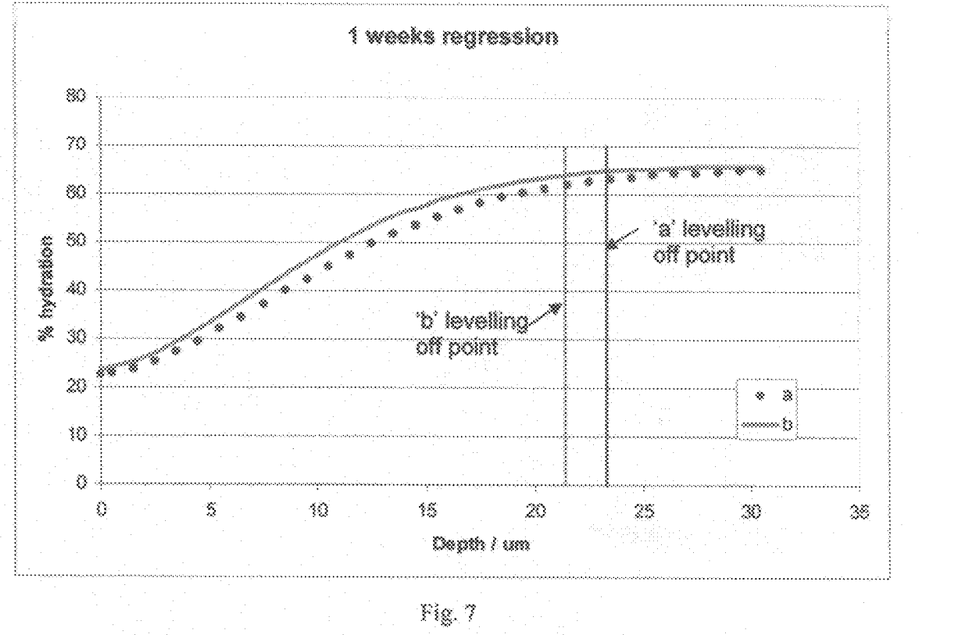
FIG. 7 shows the Raman hydration profiles (averaged across all subjects by treatment) after 1 week regression for the treatment regimes.

However if the shape of the profile at each of these time points is examined, there is a clear difference for treatment 'a' after 2 weeks usage and 1 week regression. FIGS. 6 and 7 show a change in the skin thickness as the leveling off points for treatment 'a' and 'b' are different (where as at the start of the study—the baseline reading, FIG. 4, shows that the skin at all the sites is equivalent as the leveling off points are coincident). Therefore measurement only of % hydration at a single depth beneath the surface of the SC is misleading, as treatment 'a' would have appeared to have lowered in % hydration at a fixed depth.

Figure 8:
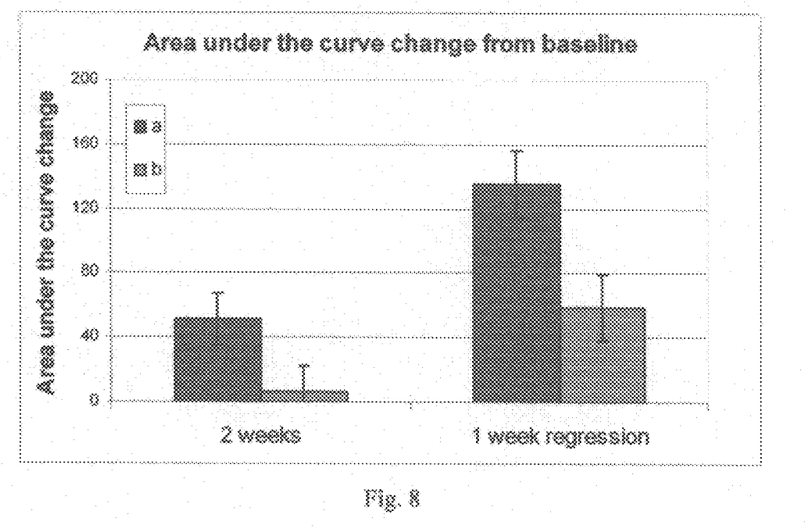
FIG. 8 shows the change from baseline in total area under the curve from the surface of the SC to the leveling off point (determined from the Raman profile) during 2 weeks of product application and 1 week regression for 2 treatment regimes.

Use of the total area under the curve calculated by taking into account the leveling off point, i.e. total hydration level within the SC is shown in FIG. 8. This shows a clear and statistically valid ($p<0.05$) increase in the total hydration within the skin (i.e. total hydration content within the SC) for treatment 'a' which was not observed by examining the % hydration at a fixed depth (the change shown corresponds to approximately a 10% increase in area under the curve is seen for product 'a'). All the data generated for this study was analysed using a gradient threshold of 0.5.

In addition to the obvious interest of the invention for dermatologic studies, it is envisaged that the invention may also be useful for generating advertising claim support for commercial skin care products. Although the invention will normally be used in a lab, it is also envisaged that the apparatus may be made mobile so as to be used in "road show" event, for example in supermarkets.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining the effectiveness of a skin care composition, comprising the steps of:
   (a) determining, using Confocal Raman Spectroscopy, a pre-application thickness of the Stratum Corneum within a test area;
   (b) applying a skin care composition to the test area;

(c) determining, using Confocal Raman Spectroscopy, a post-application thickness of the Stratum Corneum within the test area; and (d) calculating, using a computer, the effectiveness of the skin care composition; wherein the thickness of the Stratum Corneum before and after the application of the skin care composition are input as parameters when calculating the effectiveness of the skin care composition.

2. A method for determining the effectiveness of a skin care composition, comprising the steps of:

(i) selecting a Raman-active substance linked to the effectiveness of the skin care composition to be determined;

measuring the concentration profile of said Raman-active substance as a function of depth within a test area of skin using Confocal Raman Spectroscopy;

(iii) determining the pre-application thickness of the Stratum Corneum within said test area;

(iv) applying the skin care composition to said test area;

(v) measuring the concentration profile of said Raman-active substance as a function of depth within said test area using Confocal Raman Spectroscopy;

(vi) determining the post-application thickness of the Stratum Corneum within said test area; and (vii) calculating, using a computer the effectiveness of the skin care composition as a function of both:

(a) the concentration profile of the Raman-active substance before and after the application of the skin care composition; and (b) the thickness of the Stratum Corneum before and after the application of the skin care composition.

3. A method according to claim 2, wherein the thickness of the Stratum Corneum is determined by a method comprising the steps of:

(a) measuring the concentration profile of a Raman-active material as a function of depth within the test area using Confocal Raman Spectroscopy; then (b) processing the data obtained to determine the thickness of the Stratum Corneum.

4. A method according to claim 3, wherein the data is processed using the Weibull algorithm.

5. A method according to claim 2, wherein the measurement is made in vivo.

6. A method according to claim 2, wherein the Raman-active material is selected from the group consisting of water, NMF, vitamins and combinations thereof.

7. A method according to claim 6, wherein the Raman-active material is water.

8. A method according to claim 2, wherein the skin care composition comprises at least one moisturizing agent.

9. A method according to claim 2, wherein the effect to be determined is skin moisturization.

10. A method according to claim 2, wherein the Raman-active substance linked to the effectiveness of the skin care composition is water.

11. A method according to claim 2 wherein the effectiveness of the skin care composition is calculated by selecting a specific relative depth of the Stratum Corneum and comparing the amount of Raman-active substance linked to the effect to be determined present at this relative depth before and after the application of the skin care composition.

12. A method according to claim 2, wherein the effectiveness of the skin care composition is calculated by summing the amount of the Raman-active substance over the entire depth of the Stratum Corneum before the application of the skin care composition to produce a first value, by summing the amount of the Raman-active substance over the entire depth of the Stratum Corneum after the application of the skin care composition to produce a second value, and comparing the values.

13. The method according to claim 2, wherein the use of Confocal Raman Spectroscopy comprises using a probe, and wherein the computer is programmed to process the data generated by the probe.

14. An apparatus for determining the effectiveness of a skin care composition, comprising:

(a) a Confocal Raman Spectroscopy probe for generating data representing the thickness of the Stratum Corneum within a test area; and (b) a computer;

wherein the computer is programmed to:

(i) process the data generated by the probe; and (ii) calculate the effectiveness of a skin care composition based on the thickness of the Stratum Corneum before and after the application of the skin care composition.

* * * * *